United States Patent [19]

Zubovics et al.

[11] Patent Number: 5,380,724
[45] Date of Patent: Jan. 10, 1995

[54] PIPERAZINE AND HOMOPIPERAZINE DERIVATIVES, PHARMACEUTICAL COMPOSITIONS CONTAINING THEM AND PROCESS FOR PREPARING SAME

[75] Inventors: Zoltan Zubovics; Katalin Goldschmidt; Katalin Szilagyi; Ferenc Andrasi; Eszter Hodula; Lajos Toldy; Klara Sutka; Zsuzsanna Fittler; Laszlo Sebestyen; Katalin Gorgenyi; Istvan Sziraki; Jozsef Gyimesi; Valeria Vitkoczi, all of Budapest, Hungary

[73] Assignee: Gyogyszerkutato Intezet KFT, Budapest, Hungary

[21] Appl. No.: 78,601

[22] Filed: Jun. 16, 1993

[30] Foreign Application Priority Data

Jun. 17, 1992 [HU] Hungary ............... P 92 02021

[51] Int. Cl.⁶ ............... A61K 31/495; C07D 239/02; C07D 487/00; C07D 403/04
[52] U.S. Cl. ............... 514/252; 514/258; 514/259; 514/218; 540/575; 544/295; 544/238; 544/284; 544/256
[58] Field of Search ............... 540/575; 544/295, 238, 544/284, 256; 514/252, 258, 259, 218

[56] References Cited

U.S. PATENT DOCUMENTS

| | | | |
|---|---|---|---|
| 3,647,794 | 3/1972 | Regnier et al. | 544/198 |
| 3,830,811 | 8/1974 | Regnier et al. | 544/295 |
| 4,252,809 | 2/1981 | Knauf et al. | 544/260 |
| 4,778,800 | 10/1988 | Hath et al. | 514/292 |
| 5,126,356 | 6/1992 | Regnier et al. | 514/327 |

FOREIGN PATENT DOCUMENTS

| | | |
|---|---|---|
| 901850 | 6/1985 | Belgium . |
| 979894 | 12/1975 | Canada . |
| 983493 | 2/1976 | Canada . |
| 983494 | 2/1976 | Canada . |
| 983495 | 2/1976 | Canada . |
| 983497 | 2/1976 | Canada . |
| 39190 | 11/1981 | European Pat. Off. . |
| 289365 | 11/1988 | European Pat. Off. . |
| 302967 | 2/1989 | European Pat. Off. . |
| 326379 | 8/1989 | European Pat. Off. . |
| 389368 | 9/1990 | European Pat. Off. . |
| 389369 | 9/1990 | European Pat. Off. . |
| 446539 | 9/1991 | European Pat. Off. . |
| 447324 | 9/1991 | European Pat. Off. . |
| 447325 | 9/1991 | European Pat. Off. . |
| 2700073 | 7/1978 | Germany . |
| 195817 | 7/1987 | Hungary . |
| 11911 | 5/1968 | Japan . |
| 72270 | 7/1974 | Japan . |
| 72271 | 7/1974 | Japan . |
| 72272 | 7/1974 | Japan . |
| 72273 | 7/1974 | Japan . |
| 76887 | 7/1974 | Japan . |
| 149617 | 7/1987 | Japan . |
| 226843 | 9/1989 | Japan . |
| 287077 | 11/1989 | Japan . |
| 1256513 | 12/1971 | United Kingdom . |
| 1468497 | 3/1977 | United Kingdom . |
| 2155923 | 10/1985 | United Kingdom . |
| 2190084 | 11/1987 | United Kingdom . |
| 2198132 | 6/1988 | United Kingdom . |
| 07894 | 12/1987 | WIPO . |
| 7895 | 12/1987 | WIPO . |
| 7527 | 10/1988 | WIPO . |
| 8424 | 11/1988 | WIPO . |

*Primary Examiner*—Cecilia Tsang
*Attorney, Agent, or Firm*—Michael N. Meller

[57] ABSTRACT

This invention relates to novel compounds of the general formula (I) and the pharmaceutically acceptable acid addition salts thereof. In the general formula (I)

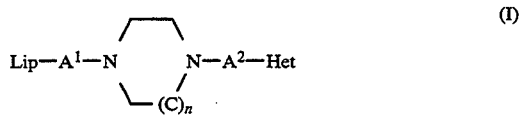

wherein Lip, $A^1$, $A^2$, Het and n are defined as in the specification. The compounds of the general formula (I) inhibit the lipid peroxidation and therefore, they are useful for the treatment or prevention of diseases and conditions wherein the inhibition of lipid peroxidation is desirable.

7 Claims, No Drawings

PIPERAZINE AND HOMOPIPERAZINE DERIVATIVES, PHARMACEUTICAL COMPOSITIONS CONTAINING THEM AND PROCESS FOR PREPARING SAME

BRIEF SUMMARY OF THE INVENTION

The present invention relates to novel piperazine and homopiperazine derivatives possessing lipid peroxidation inhibitory activity, pharmaceutical compositions containing these compounds and process for their preparation.

BACKGROUND OF THE INVENTION

It is known that the peroxidation of lipids in the living organism is a metal ion catalysed radical process playing an important role in a number of pathological conditions and diseases as well as in ageing. Such diseases and conditions related to the peroxidation of lipids are e.g. the injury of the brain and spinal cord, stroke, certain types of cerebrovascular spasms, tissue damages arising from ischemia (especially the so-called reperfusion injuries occuring during and after restoration of blood flow), furthermore myocardial infarction, atherosclerosis, inflammatory diseases, e.g. rheumatoid arthritis, various autoimmune diseases, drug toxicity, asthma and the like [see e.g. B. Halliwell, FASEB J. 1, 358 (1987) and J. M. C. Gutteridge and B. Halliwell, Methods in Enzymology 186, 1 (1990)].

An intensive research is being carried out worldwide to find on one hand substances which inhibit generally the oxidation processes in the living organism (antioxidants) while on the other hand to discover active agents specifically inhibiting the peroxidation of lipids. Compounds exerting the latter type of activity can be used in mammals, including man, for the prevention and/or treatment of diseases and conditions such as those mentioned above as being related to lipid peroxidation processes. Such drugs may have an outstanding therapeutical importance and active agents that can be used e.g. for the treatment of injuries of the central nervous system can be considered as life-saving medicaments.

Several endogenous substances inhibiting lipid peroxidation are present in the internal regulatory system of the mammalian organism, one of which is α-tocopherol, i.e. vitamin E [see e.g. M. J. Kelly in "Progress in Medicinal Chemistry" Vol. 25, p. 250, ed.: G. P. Ellis and G. B. West, Elsevier Science Publishers, 1988].

DETAILED DESCRIPTION OF THE INVENTION

The objective of the present invention was to develop novel piperazine and homopiperazine derivatives being capable to effectively inhibit lipid peroxidation and as such, being useful for the treatment of various diseases and conditions of mammals, including man, where inhibition of lipid peroxidation is desirable.

Surprisingly, it was found that this requirement is met in an outstanding manner by certain piperazine and homopiperazine derivatives bearing a six-membered nitrogen heterocyte, e.g. a substituted pyrimidine or a similar condensed heterocycle, such as a phenylpteridine which heterocycle can be bound directly or through a lower alkylene chain to one of the piperazine (or homopiperazine) nitrogen atoms while a hydrocarbyl group such as those exemplified below (or occasionally hydrogen) can be attached to the other nitrogen of the piperazine (or homopiperazine) ring. Numerous compounds have been described in the literature which consist of the above three types of structural units, i.e. an open chain or cyclic hydrocarbyl group, a piperazine ring and a substituted nitrogen heterocycle.

Such compounds show various biological effects. One of these important classes of compounds includes molecules wherein the nitrogen heterocycle mentioned above, e.g. a pyridine or pyrimidine ring substituted by amino groups as well as the hydrocarbyl group has been varied in a wide range. Thus the hydrocarbyl group may be e.g. a steroid skeleton (published PCT applications Nos. WO 87/01706 and WO 87/07895), a secosteroid (published PCT-application No. WO 88/07527) or various substituted alkyl groups of medium chain length, various mono and bicycles, e.g. a substituted phenyl, phenoxyalkyl, benzopyranyl and the like (published PCT application WO 88/08424). These classes of compounds were claimed to possess lipid peroxidation inhibitory activity. It should be noted that no such molecules bearing an alkenyl, alkanoyl, alkenoyl or an alkyl of more than 14 carbon atoms are disclosed.

In an other large group of compounds containig the three characteristic structural elements mentioned above, various types of hydrocarbyl groups being either similar to or different from those mentioned above are present, together with the nitrogen heterocycles which latter are nearly identical to those discussed in the preceeding paragraph. Thus e.g. phenyl, benzyl and benzhydryl [French patent specification No. 1,507,062, published German patent applications Nos. 1,947,332 and 2,211,738, Belgian patent specification No. 739,283 and Canadian patent specification No. 983,497 as well as the published Japanese patent application (Kokai) No. 74/76887], benzodioxolyl and benzodioxanyl [Canadian patent specifications Nos. 979,894, 983,493, 983,494 and 983,495; and the published Japanese patent applications (Kokai) Nos. 74/72270, 74/72271, 74/72272 and 74/72273], further a 3-trityl-n-propylgroup [G. L. Regnier et al., J. Med. Chem. 15, 295 (1972)] occur as characteristic structural elements. (It should be noted that no derivatives containing naphthyloxyalkyl, trityl or adamantyl attached to the piperazine nitrogen are mentioned among the above compounds.) A high number of the latter compounds has been described to show various biological effects (such as vasodilatory, sedative, analgetic, antiinflammatory and respiration promoting effects), an eventual lipid peroxidation inhibitory activity has, however, never been mentioned.

In addition to the above classes of compounds containing a piperazine ring and a further nitrogen heterocycle several other types of compounds have been published to inhibit the peroxidation of lipids. In the following some examples are given: cyclic hydroxamic acids [Y. Teshima et al., J. Antibiot. 44, 685 (1991)]; pyrimidinediones (published European patent application No. 447,324); acylamino-7-hydroxyindane derivatives [Y. Oshiro et al., J. Med. Chem. 34, 2014 (1991)]; amino analogues of vitamin C (published European patent applications Nos. 446,539 and 447,325); monocyclic analogues of vitamin E (Japanese patent specification No. 01,226,843); 4-arylthiopiperidine derivatives (published European patent application No. 433,167); 1,4-benzoquinones [e.g. G. Goto, et al. Chem. Pharm. Bull. 33, 4422 (1985)]; carboxyalkyl and hydroxyalkyl naphthoquinones [K. Okamoto et al., Chem. Pharm. Bull. 30, 2797 (1982)]; selenium compounds [A. Muller et al., Biochem. Pharmacol. 33, 3235 (1984) and A. L. Tappel, Fed. Proc. 24, 73 (1965)]; curcuminoids [S. Toda et al., J. Ethnopharmacology 23, 105 (1988)]; quinazoline derivatives (published European patent application No. 302,967); pyridylquinolines (published European patent application No. 289,365); dihydroquinoline derivatives [A. Blázovics et al., Free Radical Res. Commun. 4, 409 (1988)]; anthron and acridine derivatives [P. Frank, Biochem. Biophys. Res. Commun. 140, 797 (1986)]; dihydropyridinethiones [A. G. Odynets et al., Eksp. Med. (Riga) 21, 127 (1986); Chem. Abstr. 106, 148956]; pyrazolone derivatives (Japanese patent specification No. 62,149,617); benzothiazines (Japanese patent specification No. 01,287,077); flavonoids (see e.g. R. Campos et al., Planta Med. 55, 417 (1989)]; pyrimidopyrimidines [I. Bellido et al., Meth. Find. Exp. Clin. Pharmacol. 13, 371 (1991)]; methylated uric acid analogues [Y. Nishida, J. Pharm. Pharmacol. 43, 885 (1991)]; methylprednisolone [see e.g. H. B. Demopoulos et al., Can. J, Physiol. Pharmacol. 60, 1415 (1982)]; dehydroalanine derivatives [P. Buc-Calderon et al., Arch. Biochem. Biophys. 273, 339 (1989)]; acylated polyamines [J. M. Braughler et al., Biochem. Pharmacol. 37, 3853 (1988)].

The literature data cited above illustrate that the compounds containing a mono or diamino substituted nitrogen heterocycle attached to a piperazine ring do not necessarily inhibit lipid peroxidation and, on the other hand, the presence of the above nitrogen heterocycles is not imperative for the same biological activity.

As referred to above the desired lipid peroxidation inhibitory activity is shown also by certain novel piperazine derivatives wherein a phenylpteridine ringsystem is attached, optionally through an alkylene chain to one of the nitrogen atoms in a piperazine ring; in the most preferable compounds of this type the other nitrogen is unsubstituted.

The Belgian patent specification No. 901,850 and the published German patent application No. 2,700,073 disclose compounds of the general formula (A)

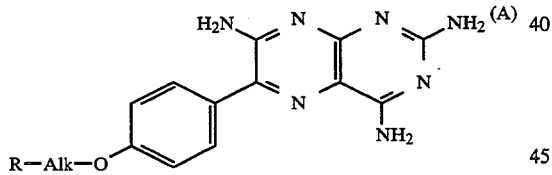

wherein R stands for a substituted amino and Alk means an optionally substituted alkylene chain. In these compounds R may be e.g. mono or dialkylamino, benzylamino or a five or six-membered heterocyclic group optionally containing one or two additional heteroatoms such as morpholinyl, piperidinyl, pyrrolidinyl or 4-methyl-1-piperazinyl. These patent specifications do not describe compounds containing piperazinyl groups being unsubstituted or substituted with a group other than methyl in position 4 as R. It has been published in the above two patent specifications as well as in papers [see e.g. H. Priewer et al., Arzneim.-Forsch./Drug Res. 35, 1819 (1985); Pharm. Res. 3, 102 (1986); Drugs of the Future 11, 669 (1986)] that the above compounds possess diuretic, potassium retaining, calcium antagonist and cardioprotective activities, but an eventual lipid peroxidation inhibitory activity was not mentioned.

In the lipid peroxidation inhibitory novel piperazine and homopiperazine derivatives of the present invention a six-membered, optionally substituted heterocycle containing two nitrogen atoms and being optionally condensed with a benzene or pyrazine ring (such as a pyrimidine, pyridazine, quinazoline or pteridine) is attached, optionally through an alkylene chain, to one of the nitrogen atoms in a piperazine (or homopiperazine) ring, while a long, open-chain hydrocarbyl group, a moiety containing two, optionally partially saturated condensed carbocycles (e.g. naphthyl) connected via an oxygen atom and a lower alkylene chain, a methyl group bearing three noncondensed unsaturated carbocycles (e.g. trityl) or a moiety consisting of three condensed saturated carbocycles (adamantyl) may be bound to the other nitrogen atom in the piperazine (or homopiperazine) ring; or the latter nitrogen may also be unsubstituted.

Accordingly, the present invention provides compounds of the general formula (I)

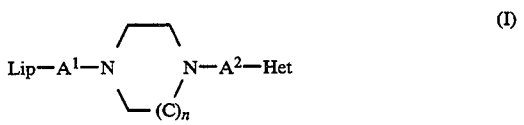

wherein

Lip stands for hydrogen; $C_{15-20}$ alkyl; $C_{10-20}$ alkanoyl or $C_{10-20}$ alkenoyl; trityl optionally substituted by halogen; adamantyl; 1- or 2-naphthyloxy or oxo-substituted tetrahydronaphthyloxy; or an amine protective group commonly used e.g. in the peptide chemistry;

$A^1$ and $A^2$ are selected independently from the group consisting of a single bond and $C_{2-3}$ alkylene optionally substituted by hydroxy or oxo;

n is 1 or 2; and

Het represents a group of the general formula (a),

wherein $R^1$ is amino or 1-pyrrolidinyl; or a 4-chloro-3-oxo-2,3-dihydro-5-pyridazinyl group of the formula (b);

or a 4-amino-6,7-dimethoxy-2-quinazolinyl group of the formula (c);

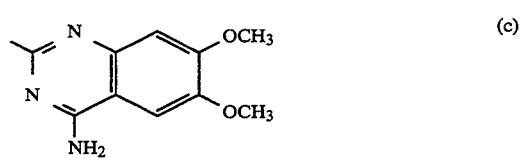

or a 4,7-diamino-6-phenyl-2-pteridinyl group of the formula (d);

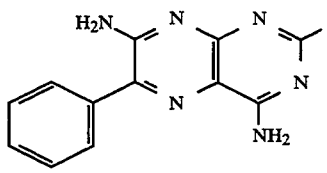

or a 2,7-diamino-6-phenyl-4-pteridinyl group of the formula (e);

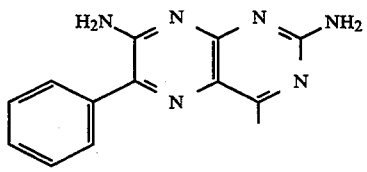

or a 2,4,7-triamino-6-pteridinylcarbonyl group of the formula (f);

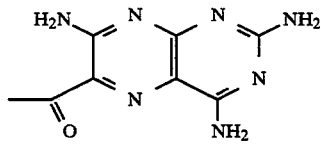

or a group of the general formula (g);

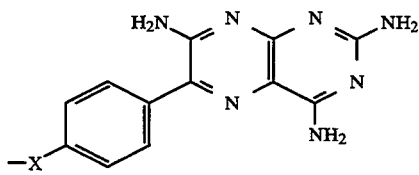

wherein X means oxygen, sulfur or nitrogen optionally substituted by lower alkyl,
with the first proviso that when Het stands for a group of the general formula (a) and both $A^1$ and $A^2$ mean single bonds then Lip may not be hydrogen;
with the second proviso that when Lip is different from naphthyloxy or oxo-substituted tetrahydronaphthyloxy then $A^1$ means a single bond;
with the third proviso that when Lip represents naphthyloxy or oxo-substituted tetrahydronaphthyloxy then $A^1$ may not be a single bond,
as well as with the fourth proviso that $A^1$ and $A^2$ cannot simultaneously stand for $C_{2-3}$ alkylene optionally substituted by hydroxy or oxo,
as well as their pharmaceutically acceptable acid addition salts and pharmaceutical compositions containing these compounds.

According to another aspect of the invention, there is provided a process for the preparation of the novel compounds of the general formula (I) and the pharmaceutically acceptable salts thereof. Due to their lipid peroxidation inhibitory effect, preferred are the compounds of the general formula (I), wherein
Lip means an open-chain or cyclic lipophilic group, e.g. a $C_{10-20}$ alkenoyl, o-chlorotrityl, 1- or 2-naphthyloxy;

$A^1$ represents a single bond, 2-hydroxy-1,3-propylene or $CH_2CO$;
$A^2$ is a single bond;
n is 1 or 2; and
Het means a group of the general formula (a).

Similarly, by virtue of their lipid peroxidation inhibitory effect, preferred are the compounds of the general formula (I), wherein
Lip means hydrogen;
$A^1$ is a single bond;
$A^2$ represents 1,3-propylene optionally substituted by hydroxy; or ethylene optionally substituted by oxo;
n is 1 or 2; and
Het stands for a group of the general formula (g), wherein X is as defined above.

Certain compounds of the general formula (I), wherein Lip means an amine protective group being commonly used in peptide chemistry, are also advantageous since they are useful intermediates in the synthesis of other compounds of the general formula (I).

The pharmaceutically acceptable acid addition salts of the compounds of the general formula (I) are salts formed with the usual known, non-toxic organic or inorganic acids, such salts include the hydrochlorides, sulfates, phosphates, tartrates, fumarates, citrates and the like.

The compounds of the present invention can be prepared by using various methods known per se. These methods differ from each other in the order of coupling of the individual structural elements of the compounds of the invention, i.e. Lip, the piperazine (or homopiperazine) ring and Het. Thus, according to the invention, the compounds of the general formula (I),

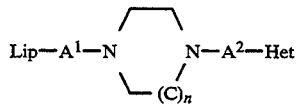

wherein Lip, $A^1$, n, $A^2$ and Het are as defined above and their pharmaceutically acceptable acid addition salts can be prepared by the following methods:

a) for preparing compounds of the general formula (I), wherein
Lip is as defined in the introduction, with the proviso that it may not be hydrogen or an amine protective group;
$A^1$ is as defined in the introduction, with the proviso that when Lip stands for naphthyloxy or oxo-substituted tetrahydronaphthyloxy then it may not be a single bond; and
n, $A^2$ and Het are as defined in the introduction,
a compound of the general formula (II),

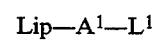

(II)

wherein
Lip and $A^1$ are as defined above and
$L^1$ is a leaving group,
is reacted with a compound of the general formula (III),

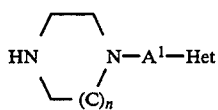 (III)

wherein
n, $A^2$ and Het are as defined above; or
b) for preparing compounds of the general formula (I), wherein
Lip means naphthyloxy or oxo-substituted tetrahydronaphthyloxy;
$A^1$ stands for 1,3-propylene substituted by hydroxy; and
n, $A^2$ and Het are as defined in the introduction,
a compound of the general formula (IV),

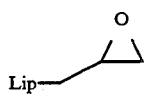 (IV)

wherein Lip is as defined above, is reacted with a compound of-the general formula (III),

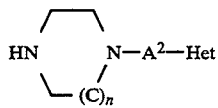 (III)

wherein
n, $A^2$ and Het are as defined above; or
c) for preparing compounds of the general formula (I), wherein
Lip is as defined in the introduction, with the proviso that it may not be hydrogen;
$A^1$ is as defined in the introduction, with the proviso that when Lip stands for naphthyloxy or oxo-substituted tetrahydronaphthyloxy then $A^1$ may not be a single bond; and with the other proviso that when Lip stands for an amine protective group then $A^1$ is a single bond; and
n, $A^2$ and Het are as defined in the introduction,
a compound of the general formula (V),

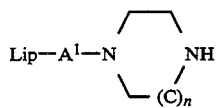 (V)

wherein
Lip, $A^1$ and n are as defined above,
is reacted with a compound of the general formula (VI), $L^2$—$A^2$—Het (VI)

wherein
$A^2$ and Het are as defined above, and
$L^2$ stands for a leaving group; or
d) for preparing compounds of the general formula (I), wherein
Lip means naphthyloxy or oxo-substituted tetrahydronaphthyloxy;
$A^1$ is as defined in the introduction, with the proviso that it may not be a single bond; and n, $A^2$ and Het are as defined for formula (I),
a compound of the general formula (VII),

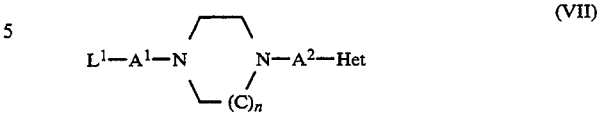 (VII)

wherein
$A^1$, n, $A^2$ and Het are as defined above, and
$L^1$ stands for a leaving group,
is reacted with a compound of the general formula
Lip—H,
wherein
Lip is as defined above; or
e) for preparing compounds of the general formula (I), wherein
Lip is as defined in the introduction, with the proviso that it may not be naphthyloxy or oxo-substituted tetrahydronaphthyloxy;
$A^1$ is a single bond;
Het stands for a group of the general formula (g),

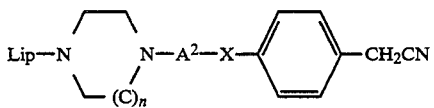 (VIII)

wherein
X is as defined in the introduction; and
n and $A^2$ are as defined above,
a compound of the general formula (VIII),

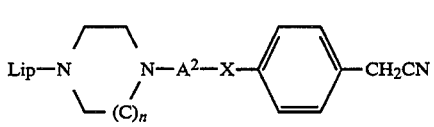 (VIII)

wherein
Lip is as defined above, with the proviso that it may not be hydrogen, naphthyloxy or oxo-substituted tetrahydronaphthyloxy;
X means oxygen, sulfur or nitrogen optionally substituted by lower alkyl; and
n and $A^2$ are as defined above,
is reacted with 5-nitroso-2,4,6-triaminopyrimidine of the formula (IX),

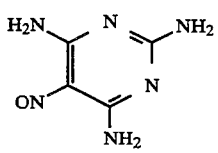 (IX)

and in the case when Lip stands for an amine protective group, this protective group is removed from the compound thus obtained; or
f) for preparing compounds of the general formula (I), wherein
Lip is as defined in the introduction, with the proviso that it may not be naphthyloxy or oxo-substituted tetrahydronaphthyloxy;
both $A^1$ and $A^2$ are single bonds;
Het stands for a group of the formula (d);

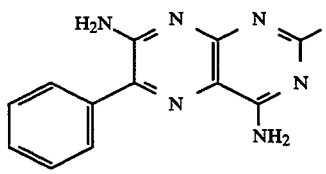

and n is as defined in the introduction,
a compound of the general formula (X),

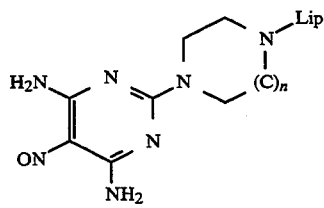

wherein
Lip is as defined above, with the proviso that it may not be hydrogen, naphthyloxy or oxo-substituted tetrahydronaphthyloxy; and
n is as defined above,
is reacted with benzyl cyanide and in the case when Lip stands for an amine protective group, this protective group is removed from the product thus obtained; or g) for preparing compounds of the general formula (I), wherein
Lip is as defined in the introduction, with the proviso that it may not be naphthyloxy or oxo-substituted tetrahydronaphthyloxy;
both $A^1$ and $A^2$ are single bonds;
Het stands for a group of the formula (e);

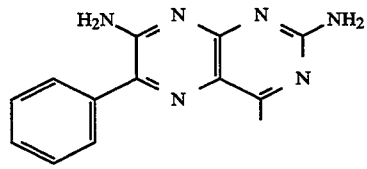

and n is as defined in the introduction,
a compound of the general formula (XI),

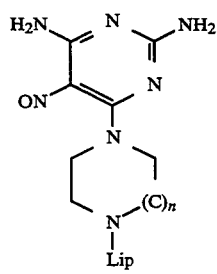

wherein
Lip is as defined above, with the proviso that it may not be hydrogen, naphthyloxy or oxo-substituted tetrahydronaphthyloxy; and
n is as defined above,
is reacted with benzyl cyanide and in the case, when Lip stands for an amine protective group, this protective group is removed from the product obtained; or h) for preparing compounds of the general formula (I), wherein
Lip is as defined in the introduction, with the proviso that it may not be naphthyloxy or oxo-substituted tetrahydronaphthyloxy;
both $A^1$ and $A^2$ are single bonds;
Het stands for a group of the formula (f);

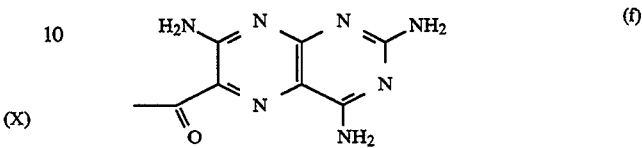

and n is as defined for formula (I),
a compound of the general formula (XII),

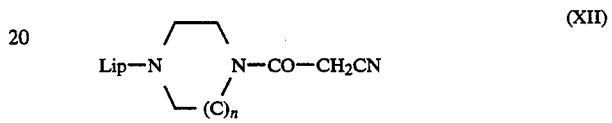

wherein
Lip is as defined above, with the proviso that it may not be hydrogen, naphthyloxy or oxo-substituted tetrahydronaphthyloxy; and
n is as defined above,
is reacted with 5-nitroso-2,4,6-triaminopyrimidine of the formula (IX)

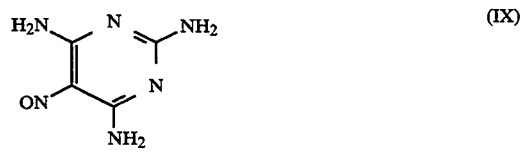

and in the case, when Lip stands for an amine protective group, this protective group is removed from the product thus obtained, and, if desired, the compound of the general formula (I) prepared by any of the above processes a)–h) is converted to its acid addition salt.

The leaving groups $L^1$ and $L^2$ in the compounds of the general formulae (II), (VI) and (VII) may independently be e.g. halogen atoms such as chlorine, bromide or iodine; or sulfonyloxy groups, e.g. methanesulfonyloxy, benzenesulfonyloxy or p-toluenesulfonyloxy.

An amine protective group as Lip in the compounds of the general formulae (V), (VIII), (X), (XI) or (XII) may be any group of this type being commonly used in the peptide chemistry; preferred protective groups are e.g. tert-butoxycarbonyl, formyl, benzyloxycarbonyl and the like.

The preferred embodiments of the above processes a)–h) will be discussed in detail hereinafter.

Process a)

The compounds of the general formula (II) are reacted with the compounds of the general formula (III) in an inert organic solvent, e.g. in a halogenated hydrocarbon such as chloroform or methylene chloride; in an alcohol such as methanol or ethanol; in an ether-like solvent such as diethyl ether or tetrahydrofuran; in acetonitrile, dimethylformamide or the like at a temperature between 0° C. and the reflux temperature of the solvent, optionally in the presence of an inorganic base, e.g. potassium carbonate or an organic base, e.g. triethylamine or pyridine. Pyridine can also be used as solvent.

The compounds of the general formula (II) used as starting substances are commercially available or can be prepared by using methods known from the literature.

It should be noted that for preparing compounds of the general formula (I), wherein Lip means alkanoyl or alkenoyl; and $A^1$ is a single bond, the acyl groups mentioned above may be introduced also by using carboxylic acids of the general formula (II) wherein $L^1$ stands for hydroxy. In such cases the reaction with the compounds of the general formula (III) is preferably carried out in the presence of a condensing agent such as carbonyldiimidazole or a carbodiimide, e.g. dicyclohexylcarbodiimide or the like.

Certain compounds of the general formula (III) are known from the literature [see e.g. the published PCT patent application No. WO 87/01706; T. H. Althuis and H. J. Hess: J. Med. Chem. 20, 146 (1977)]; while other analogues can be prepared by using the methods illustrated by the Examples hereinbelow.

Process b)

The compounds of the general formula (IV) are reacted with the compounds of the general formula (III) in an inert solvent such as an alcohol, e.g. methanol or ethanol, at a temperature between room temperature and the reflux temperature of the solvent.

The starting substances of the general formula (IV) are known from the literature or can be prepared in an analogous way [E. Fourneau and M. Trefouel, Bull. Soc. Chim. France [4], 43, 454 (1928)].

Process c)

The compounds of the general formula (V) are reacted with the compounds of the general formula (VI) under similar conditions as described for process b) above, at a temperature between 50° C. and 200° C.

The starting substances of the general formulae (V) and (VI) are known or can be prepared by analogy of the known compounds [see e.g. P. E. Aldrich et el., J. Med. Chem. 14, 535 (1971); B. Roth et. al., J. Am. Chem. Soc. 72, 1914 (1950); J. Mowry, J. Am. Chem. Soc. 75, 1909 (1953); the published German patent application No. 2,550,111 and the published PCT patent applications Nos. WO 87/01706 and WO 88/08424].

Process d)

The compounds of the general formula (VII) are reacted with the compounds of the general formula Lip—H in an inert organic solvent such as a polar solvent, e.g. acetonitrile or dimethylformamide; a halogenated hydrocarbon, e.g. chloroform or methylene chloride, optionally in the presence of an inorganic base, e.g. potassium carbonate or an organic base, e.g. triethylamine or pyridine, at a temperature between 0° C. and the boiling point of the solvent. Alternatively, a salt (e.g. alkali metal salt) of the compounds of the general formula Lip—H may be formed with a suitable base and reacted with the compound of the general formula (VII).

The starting substances of the general formula (VII) can conveniently be prepared by reaction of the appropriate compound of the general formula (III) with a compound of the general formula $L^1$—$A^1$—$L^2$, wherein $A^1$ is as defined for the general formula (I) in the introduction, with the proviso that it may not be a single bond; and $L^1$ and $L^2$ stand independently for leaving groups, under conditions described for process a) above.

Process e)

The compounds of the general formula (VIII) are reacted with 5-nitroso-2,4,6-triaminopyrimidine of the formula (IX) under the usual conditions described in the literature for the preparation of 2,4,7-triamino-6-arylpteridines [see e.g. D. J. Brown in: "Fused Pyrimidines" pages 113–120 and 359–360 in the series "The Chemistry of Heterocyclic Compounds", Eds. E. C. Taylor and A. Weissberger, John Wiley and Sons, Interscience (1988); further the Hungarian patent specification No. 195,817] in an inert solvent, such as a substituted alcohol, e.g. 2-methoxyethanol or 2-ethoxyethanol, or dimethylformamide, N-methylpyrrolidone or the like at a temperature between room temperature and the reflux temperature of the solvent, preferably at a temperature between 100° C. and 140° C., in the presence of a strong base, such as an alkali metal hydroxide, carbonate or alkoxide, e.g. sodium hydroxide, potassium carbonate or sodium 2-ethoxyethoxide.

When in process e) a compound of the general formula (I) containing an amine protective group as Lip is prepared, the protective group can be removed by any usual method known per se, e.g. in a separate reaction step. The method used for removing the protective group is chosen according to the nature of the protective group in question. Thus e.g. a tert-butoxycarbonyl may be removed in an aqueous or anhydrous medium by using a suitable acid, e.g. hydrochloric acid, formic acid or trifluoroacetic acid; benzyloxycarbonyl may be cleaved off e.g. by catalytic hydrogenation; whereas formyl may be removed by using e.g. a strong mineral acid, such as hydrochloric acid or a strong base such as an alkali metal hydroxide under heating. Alternatively, the compounds of the general formula (I) containing an amine protective group as Lip may be further reacted without isolation, i.e. the protective group may be removed in the same reaction mixture used for the preparation of the protected compound. In this case the unprotected final compounds of formula (I) wherein Lip is hydrogen are isolated and purified.

The starting compunds of the general formula (VIII) may be prepared e.g. by any of two methods illustrated by the following reaction scheme.

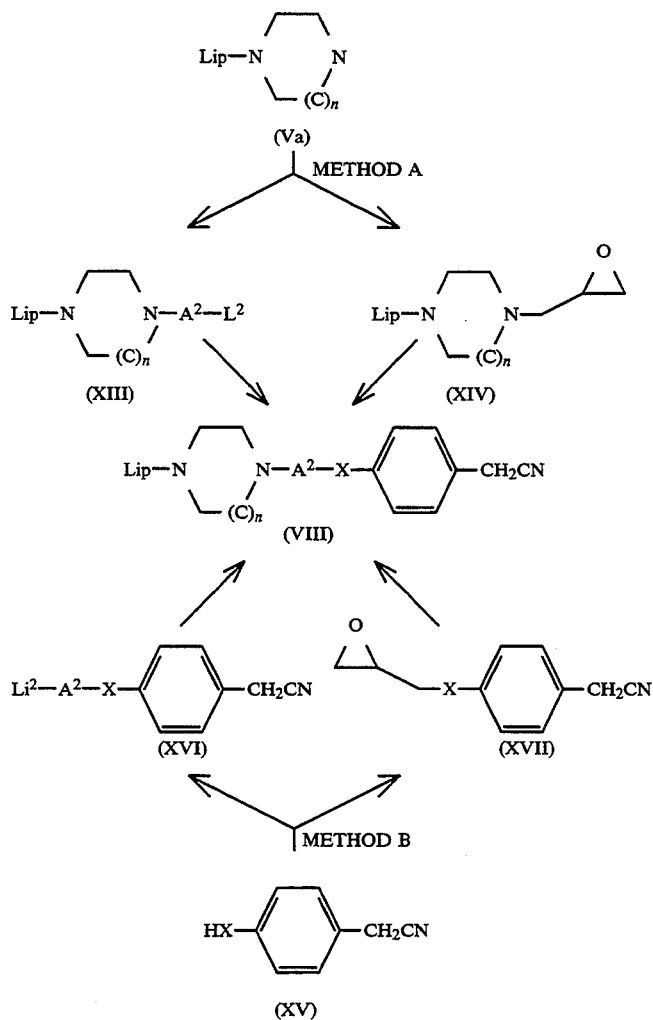

According to method A) shown in the reaction scheme, first a compound of the general formula (Va)

[i.e. a compound of the general formula (V), wherein $A^1$ is a single bond], wherein Lip and n are as defined in the introduction for the general formula (I), with the proviso that Lip may not be hydrogen, is reacted either with a compound of the general formula $L^1$—$A^2$—$L^2$, wherein $A^2$ is as defined for the general formula (I) in the introduction, with the proviso that it may not be a single bond, and $L^1$ and $L^2$ are independently leaving groups, or with epichlorohydrine e.g. under conditions described for process a) above to obtain a compound of the general formula (XIII) or (XIV)

wherein

Lip, n and $A^2$ are as defined for the general formula in the introduction, with the proviso that $A^2$ may not be a single bond; and $L^2$ means a leaving group.

Subsequently the compound of the general formula (XIII) or (XIV) thus obtained is reacted with a substituted benzyl cyanide of the general formula (XV)

wherein

X means oxygen, sulfur or nitrogen optionally substituted by lower alkyl, in an inert organic solvent, optionally in the presence of a base to obtain the desired intermediate of the general formula (VIII). Alternatively, according to method B) shown in the scheme, first a substituted benzyl cyanide of the general formula (XV), wherein X is as defined above, is reacted either with a compound of the general formula $L^1$—$A^2$—$L^2$, wherein $L^1$, $L^2$ and $A^2$ are as defined above, or with epichlorohydrine e.g. under conditions described for the above method A) in a manner known per se. Then the compound of general formula (XVI) or (XVII) thus obtained is reacted with a compound of the general formula (Va), wherein Lip and n are as defined above, to obtain the desired intermediate of the general formula (VIII).

The starting substances used in the two methods described above, i.e. the compounds of the general formulae (Va) and (XV) are known or can be prepared by using known methods as described hereinafter in the Examples. The compounds of the general formula $L^1$—$A^2$—$L^2$ are similarly known; preferred compounds of this type are e.g. 1-bromo-3-chloropropane and 2-chloroacetyl chloride.

5-Nitroso-2,4,6-triaminopyrimidine of formula (IX) used as starting substance in the present process is also known [see e.g. H. Sato et al., J. Chem. Soc. Japan, Pure Chem. Sect. 72, 866 (1951)].

Process f)

The compounds of the general formula (X) can be reacted with benzyl cyanide e.g. by using the method described in process e) and a protective group optionally present may be removed e.g. in the same way as described therein.

The starting compounds of the general formula (X) can be prepared e.g. in such a way that first a compound of the general formula (Va),

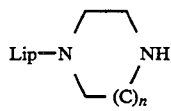

wherein
Lip and n are as defined for the general formula (I) in the introduction, with the proviso that Lip may not be hydrogen, is reacted with S-methylisothiuronium iodide in a manner described e.g. in the published European patent application No. 0,039,190 to obtain piperazinylamidine hydroiodide of the general formula (XVIII),

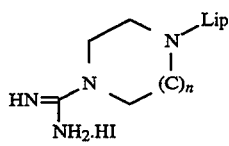

wherein
Lip and n are as defined for the formula (Va).
Subsequently a salt of the general formula (XIX),

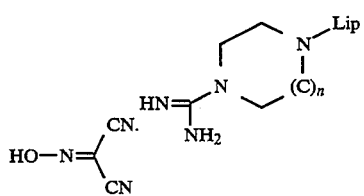

wherein
Lip and n are as defined for the formula (Va),
is formed from the compound of the general formula (XVIII) above by reaction with isonitrosomalonitrile using e.g. the method described by E. C. Taylor et al. [J. Am. Chem. Soc. 81, 2442 (1959)]. Finally the salt of the general formula (XIX) thus obtained is isomerized to the desired intermediate of the general formula (X) by heating it with a suitable base, such as an alkali metal hydroxide or alkali metal carbonate.

It should be noted that the last step (isomerization) of the preparation of compounds of the general formula (X) and the subsequent reaction with benzyl cyanide to give the compounds of the general formula (I) can conveniently be carried out in the same reaction mixture without isolation of the compound of the general formula (X), e.g. in the manner described in the Hungarian patent specification No. 195,815.

Process g)

The compounds of the general formula (XI) may be reacted with benzyl cyanide under the conditions described for process e) and a protective group eventually present may similarly be removed e.g. in the way described therein.

The starting substances of the general formula (XI) may be prepared e.g. in such a way that a compound of the general formula (XX),

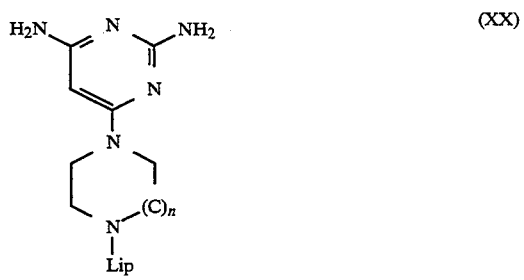

wherein
Lip and n are as defined for the general formula (I) in the introduction, with the proviso that Lip may not be hydrogen, is treated with nitrous acid by using the method described in the above-cited paper of H. Sato et. al., see the discussion of process e).

The compounds of the general formula (XX) used as starting substances can be prepared from 4-chloro-2,6-diaminopyrimidine and an appropriate compound of the general formula (Va) in a manner known per se (see the British patent specification No. 2,198,132).

Process h)

The compounds of general formula (XII) can be reacted with 5-nitroso-2,4,6-triaminopyrimidine of the formula (IX) e.g. under the conditions described for process e); and a protective group eventually present may be removed similarly to the method described therein.

The starting substances of the general formula (XII) may be prepared from ethyl cyanoacetate and the appropriate compound of the general formula (Va)

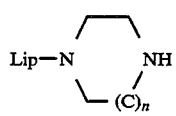

wherein
Lip and n are as defined for the compounds of the general formula (I) in the introduction,
by using known methods [see e.g. T. S. Osdene et al., J. Med. Chem. 10, 165 (1967)].

The acid addition salts of the compounds of the general formula (I) may be prepared by using any general method known per se, e.g. by reacting a base of the general formula (I) with 1-4 equivalents of the desired acid in an inert organic solvent, water or in a mixture thereof and then isolating the salt obtained by any know method (e.g. filtration, evaporation of the solvent, trituration with a solvent and/or precipitation with a non-solvent).

When a protective group is removed from a compound of the general formula (I) containing an amine protective group as Lip by using an acid, the corresponding acid addition salt of the compound of the general formula (I) containing hydrogen as Lip can directly be obtained.

The compounds of the general formula (I) of the present invention and their pharmaceutically acceptable acid addition sales are endowed with valuable biological activities. More particularly, these compounds inhibit the peroxidation of lipids and are thereby useful for the treatment and/or prevention of diseases and conditions in which the inhibition of the lipid peroxidation is desirable.

The lipid peroxidation inhibitory activity of the compounds of the present invention and of the pharmaceutically acceptable salts thereof was demonstrated and determined by biochemical and pharmacological studies. Hereinafter, several tests and the results obtained in these tests for the compounds of the invention will be described.

In these studies known lipid peroxidation inhibitors such as 3,5-di(tert-butyl)-4-hydroxytoluene ["butylated hydroxytoluene", BHT, see e.g. W. Snipes et al., Science 188, 64 (1975)], α-tocopherol (vitamin E, see e.g. the paper of M. J. Kelly cited above); further 21-[4-[2,6-di(1-pyrrolidinyl)-4-pyrimidinyl]-1-piperazinyl]-16α-methyl-pregna-1,4,9(11)-triene-3,20-dione [U74006F, see e.g. J. M. Braughler et al., J. Biol. Chem. 262, 10438 (1987)], and 2-[[4-[2,6-di(1-pyrrolidinyl)-4-pyrimidinyl]-1-piperazinyl]methyl]-6-hydroxy-2,5,7,8-tetramethyl-3,4-dihydro-2H-1-benzopyrane [U78517F, see e.g. E. D. Hall et al., J. Pharmacol. Exp. Ther. 258, 688 (1991)] were used as reference compounds.

Biochemical Investigations

1. The ferrous ion dependent lipid peroxidation inhibitory activity was measured on rat brain homogenate by using the method descibed by J. M. Braughler et al., [J. Biol. Chem. 262, 10438 (1987)] and J. A. Buege and S. D. Aust [Methods in Enzymology 52, 302 (1978)]. The $IC_{50}$ values (expressed in micromols) of some compounds of the invention and those of the reference compounds determined in this test are summarized in Table 1 below. The $IC_{50}$ value is defined as the concentration of a test substance which reduces by 50% the amount of the thiobarbituric acid reactive substances (chiefly malondialdehyde) considered to be a characteristic parameter of lipid peroxidation.

TABLE 1

| Compound (No. of Example) | $IC_{50}$, μM |
|---|---|
| Reference compounds | |
| BHT | 1 |
| α-tocopherol | 7 |
| U74006F | 39 |
| U78517F | 0.3 |
| Compounds of the invention | |
| 1 | 30 |
| 3 | 52 |
| 9 | 51 |
| 12 | 18 |
| 20 | 94 |
| 22 | 13 |
| 23 | 9 |
| 26 | 19 |
| 27 | 8 |
| 30[1)] | 12 |
| 33 | 20 |

TABLE 1-continued

| Compound (No. of Example) | $IC_{50}$, μM |
|---|---|
| 36 | 30 |

[1)]Hydrogentartrate

2. The inhibition of the ferrous ion dependent peroxidation of arachidonic acid was also measured by the method of J. M. Braughler et al. [J. Biol. Chem. 262, 10438 (1987)] and J. A. Buege and S. D. Aust [Methods in Enzymology 52, 302 (1978)]. The $IC_{50}$ values (expressed in micromols) of some compounds of the invention, further those of the reference compounds determined in this test are shown in Table 2.

TABLE 2

| Compound (No. of Example) | $IC_{50}$, μM |
|---|---|
| Reference compounds | |
| BHT | >100 |
| α-tocopherol | 2 |
| U74006F | >100 |
| U78517F | >50 |
| Compounds of the invention | |
| 37[1)] | 17 |
| 50[1)] | 15 |
| 51[1)] | 28 |
| 52[1)] | 12 |
| 53[1)] | 0.9 |
| 54[1)] | 17 |
| 57[2)] | 49 |
| 58[2)] | 38 |

[1)]Ditartrate
[2)]Hydrochloride

3. Inhibiton of the NADPH dependent lipid peroxidation was measured according to T. J. Player and A. A. Horton [J. Neurochem. 37, 422 (1981)] and Z. Duniec [Biochem. Pharmacol. 32, 2283 (1983)]. The $IC_{50}$ values (expressed in micromols) of some compounds of the invention, further those of the reference compounds determined in this test are given in Table 3.

TABLE 3

| Compound (No. of Example) | $IC_{50}$, μM |
|---|---|
| Reference compounds | |
| BHT | 2 |
| α-tocopherol | >100 |
| U74006F | >100 |
| U78517F | 0.7 |
| Compounds of the invention | |
| 23 | 13 |
| 26 | 59 |
| 27 | 22 |
| 30[1)] | 16 |

[1)]Hydrogentartrate

Pharmacological Investigations

1. The compounds of the present invention as well as the reference compounds inhibited the acute brain injury of mice described by E. D. Hall et al. [J. Neurosurg. 68, 456 (1988)]. The doses of the test compounds administered by the intravenous route and the percentage of improvement in the neurological state are summarized in Table 4.

TABLE 4

| Compound (No. of Example) | Dose, mg/kg | Improvement, % |
|---|---|---|
| Reference compounds | | |
| α-tocopherol | 30 | 97 |
| U74006F | 30 | 77 |

TABLE 4-continued

| Compound (No. of Example) | Dose, mg/kg | Improvement, % |
|---|---|---|
| U78517F | 20 | 31 |
| Compounds of the invention | | |
| 1 | 10 | 68 |
| 12 | 10 | 46 |
| 27 | 20 | 82 |
| 50[1)] | 20 | 93 |

[1)]Ditartrate

2. In the test described by D. A. Parks et al. [Surgery 92, 896 (1982)] the compounds of the invention inhibited the ischemia induced weight increase of a definite section in the small intestine of rats. The percentage of inhibition observed after administration of a 25 mg/kg oral dose of the compounds of the invention or of the reference compounds is shown in Table 5.

TABLE 5

| Compound (No. of Example) | Inhibition, % |
|---|---|
| Reference compounds | |
| α-tocopherol | — |
| U74006F | 59 |
| U78517F | 20 |
| Compounds of the invention | |
| 1 | 55 |
| 3 | 31 |
| 4 | 46 |
| 6 | 25 |
| 7 | 34 |
| 9 | 37 |
| 10 | 56 |
| 11 | 57 |
| 12 | 52 |
| 15 | 32 |
| 16 | 45 |
| 18[1)] | 31 |
| 20 | 28 |
| 23 | 52 |
| 24 | 20 |
| 25 | 35 |
| 26 | 45 |
| 27 | 60 |
| 28 | 64 |
| 30[2)] | 42 |
| 31 | 79 |
| 33 | 53 |
| 34 | 69 |
| 36 | 24 |
| 37[3)] | 35 |
| 39 | 34 |
| 50[3)] | 78 |
| 52[3)] | 34 |
| 53[3)] | 56 |
| 54[3)] | 56 |
| 55[3)] | 47 |
| 56[3)] | 44 |
| 59[3)] | 30 |

[1)]Hydrochloride
[2)]Hydrogentartrate
[1)]Ditartrate

Toxicity

The acute toxicity oft certain compounds of the invention was determined in rats and generally it was found to be favourably low. Thus e.g. a 1000 mg/kg oral dose of the compounds of Examples 1, 10, 27, 28, 34 and 50 did not provoke death of any of the treated animals (i.e. $LD_{50} > 1000$ mg/kg), similarly to the toxicity measured for the reference compound U74006F mentioned above.

The above data demonstrate that several compounds of the general formula (I) of the present invention inhibit the peroxidation of lipids in vitro. Thereby these compounds are capable to suppress various pathological processes accompanied by an increased rate of lipid peroxidation in the living organism as it was proven by the results of the above in vivo investigations. In addition, this favourable activity is accompanied by low toxicity.

For therapeutic purposes the compounds of the present invention and their pharmaceutically acceptable salts may be used alone or preferably in the form of pharmaceutical compositions. Such compositions contain as active ingredient a compound of the general formula (I) or its pharmaceutically acceptable acid addition salt in an amount which is sufficient to produce the desired effect, in admixture with known carriers, excipients, diluents and/or other additives commonly Used in the pharmaceutical practice.

The present invention also relates to a method for inhibiting the peroxidation of lipids and for treating diseases and conditions wherein the inhibition of lipid peroxidation is desirable. This method comprises of administering a therapeutically effective amount of an active ingredient of the formula (I) or of its pharmaceutically acceptable salt to a patient in need of such treatment.

Although the therapeutically effective dose of the compounds of the present invention may vary and depend upon the condition and age of each individual patient to be treated and will ultimately be determined by the attending physician, generally a daily oral dose of these compounds between about 0.1 mg and about 100 mg per kg body weight may be used for the prevention and/or treatment of diseases wherein inhibition of lipid peroxidation is desirable.

The present invention is further illustrated in detail by the following non-limiting examples.

EXAMPLE 1

1-(10-Undecenoyl)-4-[2,6-di(1-pyrrolidinyl)-4-pyrimidinyl]piperazine

To a solution of 1-[2,6-di(1-pyrrolidinyl)-4-pyrimidinyl]piperazine (2.25 g, 7.4 mmol) in anhydrous pyridine (45 ml) 10-undecenoyl chloride (1.85 ml, 1.75 g, 8.6 mmmol) was added dropwise under stirring at 0°–5° C. The reaction mixture was stirred at the same temperature for one hour and then poured into 450 ml of water. After 15 minutes of stirring the yellow powderlike precipitate was collected, washed with water and dried. Recrystallization of this crude product from acetonitrile afforded 2.86 g of the title compound, yield: 82.0%, mp. 93°–96° C.

The starting 1-[2,6-di(1-pyrrolidinyl)-4-pyrimidinyl]-piperazine can be prepared e.g. as described in the literature (published PCT application WO 87/01706).

The 1-[2,6-di(1-pyrrolidinyl)-4-pyrimidinyl]homopiperazine was prepared in a similar manner, yield: 68.4%, mp. 106°–110° C.

EXAMPLE 2

1-(n-Octadecanoyl)-4-[2,6-di(1-pyrrolidinyl)-4-pyrimidinyl]piperazine

By following the procedure of Example 1, with the difference that n-octadecanoyl chloride was used instead of 10-undecenoyl chloride, the title compound was obtained in a yield of 50.0%, mp. 102°–104° C.

EXAMPLE 3

1-(10-Undecenoyl)-4-(2,6-diamino-4-pyrimidinyl)-piperazine

A mixture of 1-(2,6-diamino-4-pyrimidinyl)piperazine-bis-trifluoroacetate (1.26 g, 3.0 mmol) and anhydrous potassium carbonate (1.38 g, 10.0 mmol) in acetonitrile (120 ml) was stirred under reflux for 30 minutes. Then 10-undecenoyl chloride (0.74 ml, 0.70 g, 3.4 mmol) was added dropwise and stirring under reflux was continued for one hour. After cooling the solvent was evaporated under reduced pressure and the residue was partitioned between methylene chloride (100 ml) and water (100 ml). The aqueous layer was separated and extracted twice with methylene chloride (40 ml each). The combined organic extracts were washed with water twice (until neutral), dried over $MgSO_4$ and concentrated under reduced pressure. The obtained crude product was triturated with isopropyl ether. In this manner 1.5 g of the title compound was obtained as a crystalline substance, yield : 69.4%, mp. 100°–104° C.

The starting 1-(2,6-diamino-4-pyrimidinyl)piperazine-bis-trifluoroacetate was prepared by following step c) of Example 60 and deprotecting thus 1-(tert-butoxycarbonyl)-4-(2,6-diamino-4-pyrimidinyl)piperazine which in turn was prepared as described in step a) of Example 59. Mp. of the obtained bis-trifluoroacenate: 192°–198° C., yield: 98.7%.

The analogous 1-(2,6-diamino-4-pyrimidinyl)-homopiperazine was prepared by reaction of 2,6-diamino-4-chloropyrimidine with unprotected homopiperazine (5 mol equivalents) in ethanol in a sealed tube, following the procedure of Example 19. Yield of the obtained base: 91.3%, mp. 62°–72° C.

EXAMPLES 4-8

By using appropriate starting compounds, the procedure of Example 3 was followed to prepare the compounds of formula (I) listed in Table 6, wherein
each of $A^1$ and $A^2$ stand for a single bond,
Lip and n are as given in the Table and
Het represents a group of the general formula (a) wherein $R^1$ is as given in the Table.

TABLE 6

| No. of Example | Lip | n | $R^1$ | Mp., °C. | Yield, % |
|---|---|---|---|---|---|
| 4 | octadecyl | 1 | $NH_2$ | 121–123 | 54.5 |
| 5 | octadecyl | 1 | 1-pyrrolidinyl | 75–77 | 68.2[1] |
| 6 | octadecanoyl | 2 | 1-pyrrolidinyl | 63–66 | 95.0[1] |
| 7 | octadecanoyl | 1 | $NH_2$ | 110–114 | 88.4 |
| 8 | 9-octadecenoyl | 1 | 1-pyrrolidinyl | 75–82 | 45.1[1] |

[1]The base form of the starting piperazine derivative was used, in the presence of 2 mol equivalents of $K_2CO_3$.

EXAMPLE 9

1-Trityl-4-(2,6-diamino-4-pyrimidinyl)piperazine

A mixture of 1-(2,6-diamino-4-pyrimidinyl)piperazine-bis-trifluoroacetate (2.1 g. 5.0 mmol), potassium carbonate (1.0 g, 7.5 mmol) and trityl chloride (1.36 g, 5.0 mmol) in acetonitrile (50 ml) was stirred vigorously at room temperature. After 3 hours the solvent was evaporated under reduced pressure and the solid residue was stirred with 100 ml of water at room temperature for one hour. The yellow powderlike substance was collected, washed with water and dried. This crude product was purified by column chromatography over silica gel eluting with a 9:1 mixture of methylene chloride and methanol to give 0.88 g of the title compound, yield: 40.4%, mp.152°–160° C.

EXAMPLE 10-14

By using appropriate starting compounds, the procedure of Example 9 was followed to prepare the compounds of formula (I) listed in Table 7, wherein
each of $A^1$ and $A^2$ stand for a single bond,
Lip and n are as given in the Table and
Het represents a group of the general formula (a) wherein $R^1$ is as given in the Table.

TABLE 7

| No. of Example | Lip | n | $R^1$ | Mp., °C. | Yield, % |
|---|---|---|---|---|---|
| 10 | trityl | 1 | 1-pyrrolidinyl | 246–250 | 33.5 |
| 11 | trityl | 2 | 1-pyrrolidinyl | 215–218 | 59.1 |
| 12 | o-chlorotrityl | 1 | $NH_2$ | 160–170 | 62.0 |
| 13 | o-chlorotrityl | 1 | 1-pyrrolidinyl | 242–250 | 54.2 |
| 14 | o-chlorotrityl | 2 | 1-pyrrolidinyl | 151–152 | 46.6 |

EXAMPLES 15-17

By using appropriate starting compounds, tile procedure of Example 9 was followed to prepare the compounds of formula (I) listed in Table 8, wherein
each of $A^1$ and $A^2$ stand for a single bond and
Lip, Het and n are as given in the Table.

TABLE 8

| No. of Example | Lip | n | Het | Mp., °C. | Yield, % |
|---|---|---|---|---|---|
| 15 | o-chlorotrityl | 1 | 4,7-diamino-6-phenyl-2-pteridinyl | 250–252 | 56.8[1] |
| 16 | o-chlorotrityl | 1 | 2,4,7-triamino-6-pteridinyl-carbonyl | >260 (dec.) | 51.6[2] |
| 17 | o-chlorotrityl | 1 | 4-amino-6,7-dimethoxy-2-quinazolinyl | 164–168 | 73.7 |

[1]Starting with the compound of Example 58
[2]Starting with the compound of Example 60

EXAMPLE 18

1-(1-Adamantyl)-4-(4-chloro-3-oxo-2,3-dihydro-5-pyridazinyl)piperazine

A mixture of 1-(1-adamantyl)piperazine (2.2 g, 10 mmol), triethylamine (1.36 ml, 10 mmol) and 4,5-dichloro-3-oxo-2,3-dihydropyridazine (1.65 g, 10 mmol) in ethanol (25 ml) was heated under reflux for 5 hours. After cooling the precipitated solids were collected, washed with ethanol and dried to afford 2.57 g of the title compound, yield: 73.6%, mp. 292°–294° C.

The above product was dissolved in a hot mixture of ethanol (25 ml), water (6 ml) and conc. HCl (2 ml), and the solution was treated with decolorizing carbon. After filtration, upon cooling the hydrochloride of the title compound separated as colorless crystals, yield: 2.0 g, mp. 306°–308° C.

EXAMPLE 19

1-(1-Adamantyl)-4-(2,6-diamino-4-pyrimidinyl)-piperazine

A mixture of 2,6-diamino-4-chloropyrimidine (0.43 g, 3.0 mmol) and 1-(1-adamantyl)-piperazine (0.66 g, 3.0 mmol) in ethanol (30 ml) was heated in a sealed tube at 170° C. for 3 hours. After cooling the solvent was removed, the solid residue was dissolved in water (45 ml) and acidified to pH=3 with conc. HCl. The obtained mixture was heated to 50° C. the insolubles were filtered off and the clear solution was rendered alkaline with 10N NaOH under stirring and cooling. The precipitated crystals were collected, washed with water until neutral and dried. In this manner 0.79 g of the title compound was obtained in the form of its monohydrate, yield: 76.6%, mp. 265°–268° C.

EXAMPLE 20

1-[2-Hydroxy-3-(1-naphthyloxy)-propyl]-4-(2,6-diamino-4-pyrimidinyl)piperazine

A mixture of 1-(2,6-diamino-4-pyrimidinyl)piperazine-bis-trifluoroacetate (0.85 g, 2.0 mmol) and potassium carbonate (0.69 g, 5.0 mmol) in ethanol (60 ml) was stirred under reflux for 30 minutes. The mixture was filtered hot and to the filtrate a solution of 1,2-epoxy-3-(1-naphthyloxy)-propane (0.6 g, 3.0 mmol) in ethanol (10 ml) was added. The mixture was heated under reflux for 3 hours, the solvent was evaporated and the residue was partitioned between ethyl acetate (80 ml) and water (80 ml). The aqueous layer was separated and extracted with ethyl acetate (40 ml). The combined organic extracts were washed once with brine, dried over MgSO4 and concentrated. The residue was chromatographed on a silica gel column eluting with a 75:20:5 mixture of ethyl acetate, methanol and conc. NH4OH. In this manner 0.58 g of the title compound was obtained as a foam, yield: 74.3%. Mp. after trituration with isopropyl ether: 122°–124° C.

The starting epoxide of formula (IV) wherein Lip stands for 1-naphthyloxy can be prepared by a known method, see E. Fourneau, M. Trefouel, Bull. Soc. chim. France [4], 43, 454 (1928).

EXAMPLES 21–30

By using appropriate starting compounds, the procedure of Example 20 was followed to prepare the compounds of formula (I) listed in Table 9, wherein A$^1$ stands for 2-hydroxy-1,3-propylene, A$^2$ stands for a single bond, Lip and n are as given in the Table and Het represents a group of the general formula (a) wherein R$^1$ is as given in the Table.

TABLE 9

| No. of Example | Lip | n | R$^1$ | Mp., °C. | Yield, % |
|---|---|---|---|---|---|
| 21 | 1-naphthyloxy | 2 | NH$_2$ | 120–125 | 39.2 |
| 22 | 1-naphthyloxy | 1 | 1-pyrrolidinyl | 132–138 | 63.4 |
| 23 | 1-naphthyloxy | 2 | 1-pyrrolidinyl | 56–58 | 61.2 |
| 24 | 2-naphthyloxy | 1 | NH$_2$ | 224–228 | 67.8 |
| 25 | 2-naphthyloxy | 2 | NH$_2$ | 57–63 | 39.3 |
| 26 | 2-naphthyloxy | 1 | 1-pyrrolidinyl | 145–147 | 48.7 |
| 27 | 2-naphthyloxy | 2 | 1-pyrrolidinyl | 102–106 | 72.9 |
| 28 | 1-oxo-1,2,3,4-tetrahydro-6-naphthyloxy | 1 | NH$_2$ | 194–197 | 28.5 |
| 29 | 1-oxo-1,2,3,4-tetrahydro-6-naphthyloxy | 1 | 1-pyrrolidinyl | 146–150 | 64.1 |
| 30 | 1-oxo-1,2,3,4-tetrahydro-6-naphthyloxy | 2 | 1-pyrrolidinyl | 182–186[1)] | 62.5 |

[1)]Hydrogentartrate 1,2-Epoxy-3-(2-naphthyloxy)-propane (mp. 51°–56° C., yield: 52.7%) and 1,2-epoxy-3-(1-oxo-1,2,3,4-tetrahydro-6-naphthyloxy)propane (oil, yield: 87.9%) used as starting compounds in Examples 24–30 were prepared by the method of E. Fourneau and M. Trefouel cited above.

EXAMPLE 31

1-[2-(1-Naphthyloxy)acetyl]-4-(2,6-diamino-4-pyrimidinyl)piperazine

A suspension of 1-(2,6-diamino-4-pyrimidinyl)piperazine-bis-trifluoroacetate (1.1 g, 2.5 mmol) and potassium carbonate (1.38 g, 10 mmol) in acetonitrile (100 ml) was stirred vigorously under reflux for 30 minutes. Then a solution of 2-(1-naphthyloxy)acetyl chloride (0.65 g, 3.0 mmol) in acetonitrile (5 ml) was added dropwise and the mixture was heated under reflux for one hour. Thereafter the insolubles were filtered off while hot and the filtrate was concentrated. The residue was stirred with 100 ml of water for one hour, the precipitate formed was collected, washed with water until neutral and dried to give 0.90 g of the title compound, yield: 59.2%, mp. 205°–210° C.

EXAMPLE 32

1-[2-(2-Naphthyloxy)acetyl]-4-[2,6-di(1-pyrrolidinyl)-4-pyrimidinyl]homopiperazine To a solution of 2-(2-naphthyloxy)acetic acid (1.1 g, 5.0 mmol) in anhydrous tetrahydrofuran (25 ml) carbonyl-diimidazole (0.80 g, 5.0 mmol) was added in portions, under stirring at room temperature. After 15 minutes a solution of 1-[2,6-di(1-pyrrolidinyl)-4-pyrimidinyl]homopiperazine (1.58 g, 5.0 mmol) in anhydrous tetrahydrofuran (15 ml) was added dropwise. The mixture was stirred at room temperature for 8 hours and the solvent was distilled off under reduced pressure. The residue was dissolved in methylene chloride, the solution was washed three times with water, dried over MgSO4 and concentrated. The obtained crude product was chromatographed over a silica gel column eluting with a 1:2 mixture of benzene and ethyl acetate to afford 0.7 g of the title compound, yield: 28%, mp. 103°–110° C.

EXAMPLE 33

1-[2-(1-Naphthyloxy)acetyl]-4-[2,6-di(1-pyrrolidinyl)-4-pyrimidinyl]piperazine

Metallic sodium (0.069 g, 3 mg-atom) was dissolved in anhydrous ethanol (4 ml) and the obtained solution was added to a mixture of 1-naphtol (0.36 g, 2.2 mmol) and 1-(2-chloroacetyl)-4-[2,6di(1-pyrrolidinyl)-4-pyrimidinyl]piperazine ((0.9 g, 2.4 mmol) in ethanol (30 ml). The reaction mixture was heated under reflux for 4 hours, cooled to room temperature and the insolubles were filtered off. The filtrate was concentrated to dryness and the residue was chromatographed over a silica gel column eluting with a 1:2 mixture of benzene and ethyl acetate. By triturating the obtained product with isopropyl ether 0.75 g of the title compound was obtained, yield: 72.0%, mp. 156°–160° C.

The starting 1-(2-chloroacetyl)-4-[2,6-di(1-pyrrolidinyl)-4-pyrimidinyl]piperazine was prepared as follows: 1-[2,6-di(1-pyrrolidinyl)-4-pyrimidinyl]piperazine (1.65 g, 5.4 mmol) was dissolved in anhydrous chloroform (30 ml), the solution was cooled to 0°–5° C. and 2-chloroacetyl chloride (0.50 ml, 0.79 g, 7.0 mmol) in anhydrous chloroform (5 ml) was added dropwise under stirring. The mixture was stirred for one hour, concentrated and the residue was dissolved in 100 ml of water. The aqueous solution was made alkaline with conc. $NH_4OH$ and stirred for one hour. During this period the separated oil solidified. The solids were collected, washed with icecold water until neutral and dried. In this manner 2.0 g of the desired chloroacetyl compound was obtained, yield: 97.0% mp. 153°–156° C.

1-(2-Chloroacetyl)-4-[2,6-di(1-pyrrolidinyl)-4-pyrimidinyl]-homopiperazine was prepared in a similar manner and was obtained as a tan viscous oil, yield: 98.2%.

EXAMPLES 34–36

By using appropriate starting compounds, the procedure of Example 31 or 32 was followed to prepare the compounds of formula (I) listed in Table 10, wherein
$A^1$ stands for $CH_2CO$,
$A^2$ stands for a single bond,
Lip and n are as given in the Table and
Het represents a group of the general formula (a) wherein $R^1$ is as given in the Table.

TABLE 10

| No. of Example | Lip | n | $R^1$ | Method (Example) | Mp., °C. | Yield, % |
|---|---|---|---|---|---|---|
| 34 | 2-naphthyloxy | 1 | $NH_2$ | 31 | 100–103 | 52.9 |
| 35 | 2-naphthyloxy | 1 | 1-pyrrolidinyl | 31 | 153–156 | 48.0 |
| 36 | 1-naphthyloxy | 2 | 1-pyrrolidinyl | 32 | 135–140 | 51.3 |

EXAMPLE 37

6-[4-[3-[4-(1-Adamantyl)-1-piperazinyl]-2-hydroxypropoxy]phenyl]-2,4,7-triaminopteridine A mixture of 4-[3-[4-(1-adamantyl)-1-piperazinyl]-2-hydroxypropoxy]benzylcyanide (3.44 g, 8.4 mmol), 5-nitroso-2,4,6-triamino-pyrimidine (1.08 g, 7.0 mmol) and 0.2N sodium-(2-ethoxyethoxide) in 2-ethoxyethanol (35 ml) was stirred at 120° C. for 30 minutes. After cooling to about 90° C. 100 ml of water was added and the mixture was cooled to room temperature followed by stirring in an ice-water bath for 30 minutes. The precipitate was collected, washed with water and acetonitrile to give the title compound (3.23 g) as a yellow powder, mp. 287°–289° C. (dec.), yield: 84.6%.

0.27 g (0.5 mmol) of the above product was dissolved in a hot solution of L(+)-tartaric acid (0.23 g, 1.5 mmol) in water (1 ml), and the obtained solution was allowed to cool. The precipitated crystals were collected, washed with acetonitrile and dried to give the ditartrate pentahydrate of the title compound, mp. 165°–175° C., yield of the salt formation: 38.3%.

The starting 4-[3-[4-(1-adamantyl)-1-piperazinyl]-propoxy]benzylcyanide was prepared as follows:

A solution of 1-(1-adamantyl)piperazine (4.4 g, 20 mmol) 4-(2,3-epoxypropoxy)benzylcyanide (2.9 g, 15.4 mmol) in methanol (45 ml) was stirred at room temperature for 4 hours. Then the solvent was removed under reduced pressure and the residue was dissolved in ethyl acetate. The solution was washed with water, dried over $MgSO_4$ and concentrated under reduced pressure. Trituration of the residue afforded 3.67 g of the desired substituted benzylcyanide as pale yellow crystals, yield: 45.8%, mp. 136°–138° C.

EXAMPLE 38

6-[4-[2-Hydroxy-3-[4-(tert-butoxycarbonyl)-1-piperazinyl]-propoxy]phenyl]-2,4,7-triaminopteridine Sodium metall (0.22 g, 9.6 mg-atom) was dissolved in 2-ethoxyethanol (60 ml) at 40°–50° C., the solution was cooled to room temperature and 5-nitroso-2,4,6-triamino-pirimidine (1.46 g, 9.5 mmol) was added, followed by 4-[2-hydroxy-3-[4-(tert-butoxy-carbonyl)-1-piperazinyl]propoxy]benzylcyanide (3.92 g, 10.4 mmol) prepared as described in Example 45. The mixture was stirred under reflux in an atmosphere of nitrogen for one hour and the obtained dark brown solution was cooled to room temperature. After dilution with 200 ml of ethyl acetate the precipitate was collected, washed with ethyl acetate and dried to yield a yellow powder, mp. 244°–246° C. (dec.). The filtrate was concentrated and the residue was dissolved in 30 ml of methanol. After treatment with decolorizing carbon the solution was concentrated to a volume of 10 ml and the separated crystals were collected. Total yield of the two generations: 84.8%.

EXAMPLES 39–44

By using appropriate starting compounds, the procedure of Example 38 was followed to prepare the compounds of formula (I) listed in Table 11, wherein
Lip is o-chlorotrityl (o—Cl—Tr) or tert-butoxycarbonyl (Boc),
$A^1$ stands for a single bond,
n and $A^2$ are as given in the Table and
Het represents a group of the general formula (g) wherein X is as given in the Table.

TABLE 11

| No. of Example | Lip | n | $A^2$ | X | Mp., °C. | Yield, % |
|---|---|---|---|---|---|---|
| 39 | o-Cl-Tr | 1 | $CH_2CH(OH)CH_2$ | O | 220–228 | 62.5[1] |
| 40 | Boc | 2 | $CH_2CH(OH)CH_2$ | O | 238–240 | 84.2 |
| 41 | Boc | 1 | $CH_2CH(OH)CH_2$ | NH | 240–241 | 45.7 |
| 42 | Boc | 1 | $CH_2CH(OH)CH_2$ | $N(CH_3)$ | 233–235 | 62.1 |
| 43 | Boc | 1 | $CH_2CH(OH)CH_2$ | S | 250–251 | 74.7[1] |
| 44 | Boc | 1 | $CH_2CO$ | NH | 275–280 | 68.3[2] |

[1] By using 4 equivalents of NaOH as base instead of sodium-(2-ethoxy-ethoxide)
[2] At 100° C.

The compounds of formula (VIII) used as staring materials in Examples 38–44 were prepared as described in Examples 45–49 below.

EXAMPLE 45

4-[2-Hydroxy-3-[4-(tert-butoxycarbonyl)-1-piperazinyl]propoxy]benzylcyanide

A solution of 4-(2,3-epoxypropoxy)benzylcyanide (2.84 g, 15 mmol) and 1-(tert-butoxycarbonyl)piperazine (4.2 g, 22.5 mmol) in methanol (35 ml) was stirred at room temperature for 3 hours and the solvent was removed. The residue was dissolved in 200 ml of ethyl acetate, washed with water, dried over MgSO$_4$ and concentrated. The obtained crude product was chromatographed on a silica gel column eluting with ethyl acetate. The obtained sticky material was triturated with hexane to give 3.95 g of the title compound, yield: 70.2%, mp. 98°–100° C.

Similarly was prepared the 4-[2-hydroxy-3-[4-(tert-butoxy-carbonyl)-1-homopiperazinyl]propoxy]benzylcyanide, it was obtained in a yield of 69.9% as an oil [starting with 1-(tert-butoxycarbonyl)homopiperazine which was in turn obtained in a yield of 38.8% as an oil by following the procedure described for the analogous piperazine derivative in the published German patent application 2,550,111].

4-[2-Hydroxy-3-[4-(o-chlorotrityl)-1-piperazinyl]-propoxy]benzylcyanide was also prepared in a similar manner, yield: 63.8%, mp. 103°–106° C. [The starting substance for the preparation of this latter compound, i.e. 1-(o-chlorotrityl)-piperazine was prepared from 1-formylpiperazine, by first alkylating with 1 mol equivalent of trityl chloride in acetonitrile in the presence of 1 mol equivalent of potasssium carbonate (3 hours at room temperature) and the obtained 1-formyl-4-(o-chlorotrityl)-piperazine (mp. 245°–247° C., yield: 89.5%) was deformylated by refluxing with an equal weight of NaOH in butanol for 90 minutes, yield: 82.0%, mp. 178°–180° C.]

EXAMPLE 46

4-[2-Hydroxy-3-[4-(tert-butoxycarbonyl)-1-piperazinyl]propyl-amino]benzylcyanide

Step a)

4-(2,3-Epoxypropyl-amino)benzylcyanide

A mixture of 4-aminobenzylcyanide (10 g, 75.7 mmol), epichlorohydrine (7.9 ml, 9.25 g, 100 mmol), ethanol (15 ml) and water (10 ml) was heated under reflux for 2 hours. After cooling the reaction mixture was poured into 100 ml of water and extracted with ether (3×50 ml). The organic extracts were combined and stirred with 50 ml of 10N NaOH at room temperature for 3 hours. The organic layer was separated, washed with water until neutral, dried over MgSO$_4$ and concentrated. The residue was chromatographed over a silica gel column eluting with a 3:1 mixture of benzene and ethyl acetate to afford 7.24 g of the title compound as an oil, yield: 51.0%.

Step b)

4-[2-Hydroxy-3-[4-(tert-butoxycarbonyl)-1-piperazinyl]propyl-amino]benzylcyanide A solution of the epoxide obtained as described in step a) above (4.96 g, 26.4 mmol) and 1-(tert-butoxycarbonyl)piperazine (6.4 g, 34.4 mmol) in methanol (30 ml) was heated under reflux for 2 hours, and the product was isolated as described in Example 45. The obtained crude product was chromatographed over a silica gel column eluting with a 9:1 mixture of ethyl acetate and methanol to give the title compound (3.68 g), mp. 86°–87° C., yield: 37.2%.

EXAMPLE 47

4-[N-Methyl-N-[2-hydroxy-3-[4-(tert-butoxycarbonyl)-1-piperazinyl]propyl]amino]benzylcyanide

Step a)

4-[N-Methyl-N-(2,3-epoxypropyl)amino]benzylcyanide

A mixture of 4-methylaminobenzylcyanide (3.05 g, 20.9 mmol), epichlorohydrine (2.4 ml, 2.87 g, 31 mmol), ethanol (25 ml) and water (20 ml) was heated under reflux for 3 hours. After cooling the mixture was diluted with ethanol (10 ml) followed by addition of aqueous 10N NaOH (6 ml). The obtained clear solution was stirred at room temperature for one hour and the ethanol was distilled off. The residue was diluted with 100 ml of water and extracted with ether (3×50 ml). The organic extracts were washed with brine until neutral, dried over MgSO$_4$ and concentrated. The residue was chromatographed over a silica gel column eluting with a 3:1 mixture of benzene and ethyl acetate to give 2.21 g of the oily title compound, yield: 52.2%.

Step b)

4-[N-Methyl-N-[2-hydroxy-3-[4-(tert-butoxycarbonyl)-1-piperazinyl]propyl]amino]benzylcyanide The epoxide prepared as described in step a) above (2.21 g, 10.9 mmol) was allowed to react with 1-(tert-butoxycarbonyl)piperazine (3.05 g, 16.4 mmol) by following the procedure of step b) of Example 46 and the product was isolated as described therein. In this manner 4.02 g of the title compound was obtained as an oil, yield: 94.8%.

EXAMPLE 48

4-[2-Hydroxy-3-[4-(tert-butoxycarbonyl)-1-piperazinyl]propyl-thio]benzylcyanide

Step a)

4-(N,N-Dimethylthiocarbamoyloxy)benzylcyanide

Metallic sodium (1.15 g, 50 mg-atom) was dissolved in methanol (100 ml) and 4-hydroxybenzylcyanide (6.7 g, 50 mmol) was added. The obtained solution was concentrated and acetonitrile (2×10 ml) was evaporated from the residue. The obtained salt was dissolved in anhydrous dimethylformamide (200 ml) and about 25 ml of the solvent was removed under reduced pressure. To the obtained solution N,N-dimethylthiocarbamoyl chloride (9.9 g, 80 mmol) was added and the reaction mixture was stirred at 80°–85° C. for 2 hours. Thereafter additional N,N-dimethylthiocarbamoyl chloride (2.5 g, 20 mmol) was added and stirring at 80° C. was continued for further one hour. After cooling the mixture was poured into aqueous 1% KOH (500 ml) and extracted with ether (3×200 ml). The organic extracts were washed with water until neutral, dried over MgSO$_4$ and concentrated. The solid residue was triturated with water and after drying also with isopropyl ether to give the title compound (5.42 g), mp. 120°–124° C., yield: 52.7%.

Step b)

4-(N,N-Dimethylcarbamoylthio)benzylcyanide

To Dowtherm A (75 ml) preheated to 250° C., under nitrogen the compound prepared as described in step a) above (5.05 g, 22.9 mmol) was added and the mixture was stirred at the same temperature for one hour. After cooling the reaction mixture was diluted with 200ml of benzene, treated with decolorizing carbon and the solvents were distilled off under reduced pressure. The residue was chromatographed on a silica gel column eluting with a 3:1 mixture of benzene and ethyl acetate to afford the title compound (3.08 g) as yellow crystals, yield: 60.1%, mp. 97°–99° C.

Step c)

1-(2,3-Epoxypropyl)-4-(tert-butoxycarbonyl)piperazine

A solution of 1-(tert-butoxycarbonyl)piperazine (18.6 g, 100 mmol) and epichlorohydrine (10.2 ml, 12.0 g, 130 mmol) in methanol (50 ml) was stirred at room temperature for 24 hours and the solvent was evaporated. The residue was dissolved in 200 ml of ether and the solution was stirred with 10N aqueous NaOH (100 ml) at room temperature for 2 hours. Then the organic layer was separated, washed with brine until neutral, dried over $MgSO_4$ and concentrated to afford the title compound (21.8 g) as a pale yellowish viscous oil, yield: 90.1%.

Step d)

4-[2-Hydroxy-3-[4-(tert-butoxycarbonyl)-1-piperazinyl]propyl-thio]benzylcyanide A mixture of the product of step b) above (3.08 g, 14 mmol), the epoxide prepared as described in step c) above (3.4 g, 14 mmol), ethanol (70 ml) and 2N aqueous NaOH (7 ml) was heated under reflux in an atmosphere of nitrogen for 2 hours. After cooling the mixture was poured into 300 ml of water and extracted with ethyl acetate (2×150 ml). The organic layer was washed with brine until neutral, dried over $MgSO_4$ and concentrated. The residue was chromatographed on a silica gel column eluting with ethyl acetate to give 1.69 g of the title compound as a colorless solid, yield: 30.8%. Mp. after trituration with hexane: 69°–70° C.

EXAMPLE 49

4-[2-[4-(Tert-butoxycarbonyl)-1-piperazinyl]acetylamino]benzylcyanide

Step a)

4-(2-Chloroacetylamino)benzylcyanide

2-Chloroacetyl chloride (3.3 ml, 5.0 g, 44 mmol) was added dropwise at 10°–15° C. to a solution of 4-aminobenzylcyanide (5.3 g, 40 mmol) in dimethyl acetamide (20 ml) and the mixture was stirred at room temperature for one hour. After pouring into water the precipitate was collected, washed with water and dried over $P_2O_5$ under reduced pressure to give the title compound (7.33 g) as nearly colorless crystals, yield: 87.8%, mp 124°–125° C.

Step b)

4-[2-[4-(Tert-butoxycarbonyl)-1-piperazinyl]acetylamino]benzyl-cyanide

A mixture of the product obtained according to step a) above (2.1 g, 10 mmol), 1-(tert-butoxycarbonyl)piperazine (2.4 g, 13 mmol) and potassium carbonate (1.8 g, 13 mmol) in acetonitrile (50 ml) was stirred under reflux for 2 hours. After cooling the mixture was poured into water. The precipitate was collected, washed with water and dried under reduced pressure over $P_2O_5$ to afford 3.48 g of the title compound as nearly colorless crystals, yield: 97.2%, mp 137°–138° C.

EXAMPLE 50

6-[4-[2-Hydroxy-3-(1-piperazinyl)propoxy]phenyl]-2,4,7-triamino-pteridine

Method A)

A mixture of the protected compound obtained according to Example 38 (5.5 g, 10.8 mmol) and 10% aqueous HCl (140 ml) was stirred at room temperature for 20 hours. The yellow suspension was diluted with 350 ml of water and heated to about 40° C. The obtained solution was filtered and made alkaline with 5N aqueous NaOH. The formed precipitate was collected, washed with water until neutral and dried to give the title compound (4.4 g) as pale yellow crystals, yield: 100%, mp. 245°–255° C.

3.91 g (9.5 mmol) of the above product was added to a solution of L(+)-tartaric acid (3.54 g, 23.6 mmol) in water (60 ml) and the solids were dissolved by heating to reflux. The hot solution was treated with decolorizing carbon, filtered and allowed to cool. The separated crystals were collected, washed with water and acetonitrile and dried to give the ditartrate-trihydrate of the title compound, mp. 185°–190° C., yield of the salt formation: 66.9%.

Method B)

A suspension of the protected compound obtained according to Example 38 (1.5 g, 3 mmol) in a 1.5N solution of HCl in ethyl acetate (20 ml) was stirred for 5 hours at room temperature. The solids (HCl salt of the title product) were then collected and after drying dissolved in water. The solution was made alkaline with aqueous 5N NaOH and the precipitated base was filtered off to give the title compound which was identical with the product obtained according to Method A) above, yield: 37.0%.

Method C)

A mixture of the protected compound obtained according to Example 38 (0.26 g, 0.5 mmol) and L(+)-tartaric acid (0.23 g, 1.5 mmol) in water (2.5 ml) was heated under reflux for one hour and allowed to cool to room temperature. The separated precipitate was collected to give the ditartrate-trihydrate of the title compound which was identical with the salt obtained according to Method A) above, yield: 65.8%, mp 169°–175° C.

EXAMPLES 51–55

By using the appropriate starting compounds prepared according to Examples 40–44, the procedure of Example 50 was followed to prepare the compounds of formula (I) listed in Table 12, wherein Lip is hydrogen, $A^1$ stands for a single bond, n and $A^2$ are as given in the Table and Het represents a group of the general formula (g) wherein X is as given in the Table.

TABLE 12

| No. of Example | n | $A^2$ | X | Method (Example) | Mp., °C.[1] | Yield, % |
|---|---|---|---|---|---|---|
| 51 | 2 | $CH_2CH(OH)CH_2$ | O | 50/B | 163–168 | 48.6[2] |
| 52 | 1 | $CH_2CH(OH)CH_2$ | NH | 50/A | 205–210[3] | 55.9 |
| 53 | 1 | $CH_2CH(OH)CH_2$ | $N(CH_3)$ | 50/B | 175–180[4] | 68.1 |
| 54 | 1 | $CH_2CH(OH)CH_2$ | S | 50/B | 250–253[3] | 61.2 |
| 55 | 1 | $CH_2CO$ | NH | 50/B | 90–95[5] | 45.1 |

[1]Ditartrate
[2]By using 97% HCOOH instead of HCl
[3]Dihydrate;
[4]Pentahydrate;
[5]Heptahydrate

EXAMPLE 56

6-[4-[3-(1-Piperazinyl)propylamino]phenyl]-2,4,7-triamino-pteridine

A mixture of 4-[3-(4-formyl-1-piperazinyl)-propylamino]benzylcyanide (1.15 g, 4.0 mmol), 5-nitroso-2,4,6-triamino-pyrimidine (0.56 g, 3.6 mmol) and 0.2N sodium-(2-ethoxy-ethoxide) in 2-ethoxyethanol (18 ml) was stirred under reflux for 3 hours, then NaOH (0.14 g, 3.5 mmol) was added and stirring under reflux was continued for further 2.5 hours. After cooling the mixture was diluted with 100 ml of ether. The separated precipitate was collected, washed with ether, then with water and dried to afford the title compound (0.92 g) as a yellow powder, yield: 64.8%. The above product was dissolved in a hot solution of L(+)-tartaric. acid (0.75 g, 5 mmol) in water (6 ml) and after cooling the mixture was diluted with methanol (6 ml). The separated crystals were collected, washed with methanol and dried to give the ditartrate of the title compound, mp. 170°–178° C. Yield of the salt formation: 51.9%.

The starting 4-[3-(4-formyl-1-piperazinyl)-propylamino]benzylcyanide was prepared as follows:

Step a)

1-Formyl-4-(3-chloropropyl)piperazine

A mixture of 1-formylpiperazine (5.7 g, 50 mmol), 1-bromo-3-chloropropane (7.2 ml, 11.8 g, 75 mmol) and chlorobenzene (30 ml) was stirred at 100°–105° C. for 3 hours. After cooling the separated 1-formylpiperazine hydrochloride (4.58 g, yield: 94.4%) was filtered off and the filtrate concentrated. The residue was chromatographed on a silica gel column eluting with a 8:2 mixture of ethyl acetate and methanol to afford 2.46 g of the oily title compound, yield: 51.6%.

Step b)

4-[3-(4-Formyl-1-piperazinyl)propylamino]benzylcyanide

A mixture of 1-formyl-4-(3-chloropropyl)piperazine (1.0 g, 5.2 mmol) prepared according to step a) above, 4-aminobenzylcyanide (0.66 g, 5 mmol) and sodium iodide (0.15 g, 1 mmol) was heated at 100°–105° C. for 2 hours. After cooling the mixture was dissolved in 40 ml of water and treated with decolorizing carbon. The filtered solution was made alkaline with 2N aqueous NaOH and extracted with chloroform (3×20 ml). The organic extracts were washed with water, dried over $MgSO_4$ and concentrated. The residue was chromatographed on a silica gel column eluting with a 2:1 mixture of ethyl acetate and methanol to give the title compound. Yield: 0.55 g, 38.5%. Mp. after trituration with ether: 85°–87° C.

EXAMPLE 57

1-(1-Adamantyl)-4-(4,7-diamino-6-phenyl-2-pteridinyl)-piperazine

Step a)

1-(1-Adamantyl)-4-amidinopiperazine hydroiodide

The title compound was prepared as described for 1-formylpiperazine in Example 1 of the published European patent application No. 39,190, starting with 1-(1-adamantyl)piperazine and S-methyl-isothiourea hydroiodide, mp. 278°–280° C., yield: 72.3 %.

Step b)

Isonitrosomalonitrile salt of 1-(1-adamantyl)-4-amidinopiperazine

A solution of sodium nitrite (0.74 g, 10.5 mmol) in water (1 ml) was added dropwise at 0°–5° C. to a mixture of malonitrile (0.66 g, 10 mmol), water (1.2 ml) and acetic acid (0.7 ml) and the mixture was stirred first at the same temperature for 2 hours and then at room temperature for further 3 hours. Thereafter the reaction mixture was heated to 50° C. and a mixture of the hydroiodide prepared according to step a) above (3.12 g, 80 mmol) in methanol (6 ml), made alkaline with a 2N ethanolic NaOEt solution was added. The obtained mixture was stirred at 80°–85° C. for 2 hours, the insolubles were filtered off while hot, and the filtrate was concentrated. Trituration of the residue with water afforded 2.40 g of the crude title product, yield: 83.9%. This crude product was dissolved in acetone, the insolubles were filtered off and the filtrate was concentrated to dryness to give the title compound in pure state, mp. 182°–186° C.

Step c)

1-(1-Adamantyl)-4-(4,7-diamino-6-phenyl-2-pteridinyl)-piperazine

To a solution of the salt prepared as described in step b) above (0.50 g, 1.4 mmol) in 2-ethoxyethanol (7 ml) potassium carbonate (0.13 g, 0.9 mmol) was added and the mixture was heated under reflux for 90 minutes. After cooling to about 60° C. NaOH (0.08 g, 2 mmol) was added followed by the dropwise addition of benzylcyanide (0.25 ml, 2.2 mmol) in 2-ethoxyethanol (2 ml) at the same temperature. The mixture was stirred at 80° C. for 2 hours, cooled and diluted with 50 ml of water. The obtained precipitate was collected, washed with water and acetone to give the title compound (0.37 g), yield: 57.8%, mp. 293°–297° C. (dec.).

The above product was converted to its hydrochloride by using an ethyl acetate solution of anhydrous HCl, mp.>231° C. (dec.).

EXAMPLE 58

1-(4,7-Diamino-6-phenyl-2-pteridinyl)piperazine

Step a)

1-(Tert-butoxycarbonyl)-4-amidinopiperazine hydroiodide

The title compound was prepared as described for 1-formylpiperazine in Example 1 of the published European patent application No. 39,190, starting with 1-(1-tert-butoxycarbonyl)piperazine and S-methyl-isothiourea hydroiodide, mp. 180°–182° C., yield: 66.3%.

Step b)

Isonitrosomalonitrile salt of 1-(tert-butoxycarbonyl)-4-amidinopiperazine

The title compound was prepared by following the procedure described in step b) of Example 57, starting with the hydroiodide obtained according to step a) above, yield: 85.5%, mp. 155°–162° C.

Step c)

1-(Tert-butoxycarbonyl)-4-(4,7-diamino-6-phenyl-2-pteridinyl)-piperazine

The title compound was prepared by following the procedure described in step c) of Example 57, starting with the salt obtained according to step b) above, yield: 40%, mp. 240°–242° C.

Step d)

1-(4,7-Diamino-6-phenyl-2-pteridinyl)piperazine

A mixture of the protected compound prepared according to step c) above (3.8 g, 9 mmol) and 97% formic acid (20 ml) was stirred at room temperature for 5 hours. The mixture was then poured into 200 ml of water and the pH was adjusted to 10 with 10N NaOH. The separated solids were collected, dried and recrystallized from acetonitrile to afford the title compound (1.63 g), yield: 56.2%, mp. 244°–247° C.

The above product was converted to its hydrochloride by using an ethyl acetate solution of anhydrous HCl, mp. 233°–236° C.

EXAMPLE 59

1-(2,7-Diamino-6-phenyl-4-pteridinyl)piperazine

Step a)

1-(Tert-butoxycarbonyl)-4-(2,6-diamino-4-pyrimidinyl)-piperazine

A mixture of 2,6-diamino-4-chloropyrimidine (2.88 g, 20 mmol) and 1- (tert-butoxycarbonyl)piperazine (5.6 g, 30 mmol) in chlorobenzene (30 ml) was stirred under reflux for 3 hours. After cooling the formed precipitate was collected and stirred with aqueous 1N NaOH (63 ml) at room temperature for 15 minutes. The solids were collected, washed with water and dried, yield: 90.4%, mp. 176°–179° C.

Step b)

1-(Tert-butoxycarbonyl)-4-(2,6-diamino-5-nitroso-4-pyrimidinyl)-piperazine

A solution of sodium nitrite (4.24 g, 64.6 mmol) in water (43 ml) was added dropwise under 10° C. to a mixture of the product obtained according to step a) above (18.1 g, 64.6 mmol), and acetic acid (180 ml). The mixture was stirred for one hour and the precipitate was collected. This product was stirred with an aqueous 10% solution of potassium carbonate (230 ml) at room temperature for one hour. The formed pink solids were collected, washed with water and dried at 100° C., yield: 94.8%, mp. 235°–240° C. (dec.).

Step c)

1-(Tert-butoxycarbonyl)-4-(2,7-diamino-6-phenyl-4-pteridinyl)-piperazine

The title compound was prepared by reaction of the product obtained as described in step b) above with benzylcyanide, following the procedure of Example 37 with the difference that instead of sodium-(2-ethoxyethoxide) NaOH was used as a base. Mp. 245°–246° C., yield: 54.7%.

Step d)

1-(2,7-Diamino-6-phenyl-4-pteridinyl)piperazine

By following Method B) of Example 50 deprotection of the compound obtained according to step c) above the title compound was obtained in a yield of 83.0%, mp.(base) 265°–275° C.

The above product was converted to its ditartrate by following Method A) of Example 50, mp. 150°–155° C.

EXAMPLE 60

1-(2,4,7-Triamino-6-pteridinylcarbonyl)piperazine

Step a)

1-(Tert-butoxycarbonyl)4-(2-cyanoacetyl)piperazine

A mixture of 1-(tert-butoxycarbonyl)piperazine (37.25 g, 0.20 mol) and ethyl cyanoacetate (22.6 g, 0.20 mol) was beamed at 150°–155° C. for 3 hours. After cooling the mixture solidified. Trituration with isopropyl ether afforded 24.7 g of the title compound, mp. 143°–145° C., yield: 48.8%.

Step b)

1-(Tert-butoxycarbonyl)-4-(2,4,7-triamino-6-pteridinylcarbonyl)-piperazine

The title compound was prepared by following the procedure described in Example 37, by reaction of the compound obtained according to step a) above with 5-nitroso-2,4,6-triaminopyrimidine. Yield: 59.1%, mp. 245°–250° C.

Step c)

1-(2,4,7-Triamino-6-pteridinylcarbonyl)piperazine

The protected compound obtained as described in step b) above was stirred with twofold (v/w) trifluoroacetic acid at 5°–10° C. for one hour, diluted with tenfold (v/v) methanol and the precipitate was collected. In this manner the bis-trifluoroacetate of the title compound was obtained, mp. 233°–238° C., yield: 69.8%.

We claim:

1. A compound selected from the group consisting of that of the formula (I), $$\text{Lip}-A^1-N\underset{(C)_n}{\overset{\frown}{\underset{\smile}{\bigg)}}}N-A^2-\text{Het} \qquad (I)$$

and the pharmaceutically acceptable salts thereof wherein

Lip is selected from the group consisting of hydrogen $C_{15-20}$ alkyl, $C_{10-20}$ alkanoyl, $C_{10-20}$ alkenoyl, unsubstituted trityl, trityl substituted by halogen, adamantyl, 1-naphthyloxy, 2-naphthyloxy, oxo-substituted tetrahydronaphthyloxy and an amine protective group commonly used in the peptide chemistry;

$A^1$ and $A^2$ are the same or different and are selected from the group consisting of a single bond, $C_{2-3}$ alkylene, hydroxy-substituted $C_{2-3}$ alkylene and oxo-substituted $C_{2-3}$ alkylene;

n is 1 or 2; and

Het is selected from the group consisting of 1) a group of the formula (a),

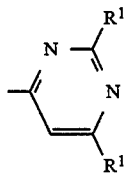

wherein $R^1$ is amino or 1-pyrrolidinyl;

2) a 4-chloro-3-oxo-2,3-dihydro-5-pyridazinyl group of the formula (b);

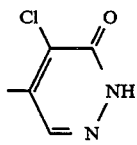

3) a 4-amino-6,7-dimethoxy-2-quinazolinyl group of the formula (c);

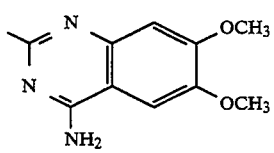

4) a 4,7-diamino-6-phenyl-2-pteridinyl group of the formula (d);

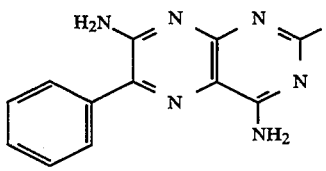

5) a 2,7-diamino-6-phenyl-4-pteridinyl group of the formula (e);

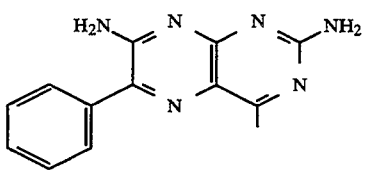

6) a 2,4,7-triamino-6-pteridinylcarbonyl group of the formula (f);

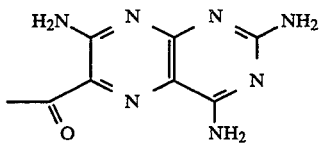

and 7) a group of formula (g);

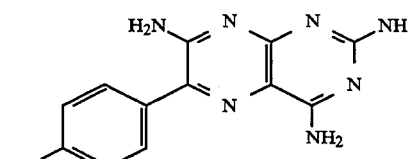

wherein X is selected from the group consisting of oxygen, sulfur, nitrogen lower alkyl-oxygen, lower alkyl nitrogen and lower alkyl sulfur with a first proviso that when Het stands for a group of the formula (a) and both $A^1$ and $A^2$ are single bonds then Lip is not hydrogen;

with a second proviso that when Lip is different from naphthyloxy or oxo-substituted tetrahydronaphthyloxy then $A^1$ is a single bond;

with a third proviso that when Lip represents naphthyloxy or oxo-substituted tetrahydronaphthyloxy then $A^1$ may not be a single bond, as well as with a fourth proviso that $A^1$ and $A^2$ cannot simultaneously be hydroxy-substituted-$C_{2-3}$ alkylene or oxo-substituted $C_{2-3}$-alkylene and their salts.

2. A compound selected from the group consisting of 1-(10-undecenoyl)-4-[2,6-di(1-pyrrolidinyl)-4-pyrimidinyl]piperazine, 1-[2-hydroxy-3-(2-naphthyloxy) propyl]-4-[2,6-di(1-pyrrolidinyl)-4-pyrimidinyl]homopiperazine, 6-[4-[2-hydroxy-3-(1-piperzinyl)propoxy]phenyl]-2,4,7-triaminopteridine,6-[4-[N-methyl-N-[2-hydroxy-3-(1-piperazinyl)propyl]amino]-phenyl]-2,4,7-triaminopteridine and the pharmaceutically acceptable salts thereof.

3. A pharmaceutical composition for inhibiting lipid peroxidation which comprises as active ingredient a lipid peroxidation inhibiting amount of a compound of the formula (I) wherein Lip, $A^1$, $A^2$, Het and n are as defined in claim 1, or a pharmaceutically acceptable acid addition salt thereof in admixture with pharmaceutically acceptable carriers and, when required, pharmaceutically acceptable additives.

4. A process for preparing a pharmaceutical composition which comprises mixing, as active ingredient, a compound of the formula (I) as defined in claim 1 or a pharmaceutically acceptable acid addition thereof, with one or more pharmaceutically acceptable additives, carriers or additives, and carriers.

5. Method for the treatment of a patient suffering from a disease and condition resulting from pathological peroxidation processes occurring in the living organism, which comprises administrating to said patient a therapeutically effective amount of a compound of the general formula (I) as defined in claim 1.

6. A method according to claim 5 for the treatment or prevention of diseases and conditions in a patient where the inhibition of lipid peroxidation is desirable, which comprises administering to said patient, a therapeutically effective amount of a compound of the general formula (I) as defined in claim 1, or a pharmaceutically acceptable salt thereof.

7. 6-[4-[2-Hydroxy-3-(1-piperazinyl) propoxy]-phenyl]-2,4,7-triamino-pteridine, a compound according to claim 1.

* * * * *

UNITED STATES PATENT AND TRADEMARK OFFICE
CERTIFICATE OF CORRECTION

PATENT NO. : 5,380,724
DATED : January 10, 1995
INVENTOR(S) : Zubovics et al

It is certified that error appears in the above-indentified patent and that said Letters Patent is hereby corrected as shown below:

Column 36, Line 59, claim 5, after "claim 1" insert
-- or a pharmaceutically acceptable salt thereof --

Signed and Sealed this

Fourth Day of April, 1995

Attest:

BRUCE LEHMAN

Attesting Officer — Commissioner of Patents and Trademarks